United States Patent
Makino et al.

(10) Patent No.: US 10,917,615 B2
(45) Date of Patent: Feb. 9, 2021

(54) ENDOSCOPE SYSTEM, RECEIVING DEVICE, WORKSTATION, SETTING METHOD, AND COMPUTER READABLE RECORDING MEDIUM

(71) Applicant: OLYMPUS CORPORATION, Tokyo (JP)

(72) Inventors: Yuta Makino, Chofu (JP); Katsuyoshi Taniguchi, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 5 days.

(21) Appl. No.: 16/426,165

(22) Filed: May 30, 2019

(65) Prior Publication Data

US 2019/0281258 A1  Sep. 12, 2019

Related U.S. Application Data

(63) Continuation of application No. PCT/JP2017/036424, filed on Oct. 6, 2017.

(30) Foreign Application Priority Data

Dec. 7, 2016  (JP) ................................ 2016-237604

(51) Int. Cl.
*A61B 1/04* (2006.01)
*H04N 7/18* (2006.01)
(Continued)

(52) U.S. Cl.
CPC .............. *H04N 7/181* (2013.01); *A61B 1/00* (2013.01); *A61B 1/0002* (2013.01);
(Continued)

(58) Field of Classification Search
CPC ......... H04W 76/10; H04N 7/181; H04N 5/77; H04N 7/183
See application file for complete search history.

(56) References Cited

U.S. PATENT DOCUMENTS

2008/0318540 A1  12/2008  Homan et al.
2010/0041950 A1*  2/2010  Oda ........................ G16H 40/20
600/109

(Continued)

FOREIGN PATENT DOCUMENTS

JP  2006-006487 A  1/2006
JP  2007-068895 A  3/2007
(Continued)

OTHER PUBLICATIONS

International Search Report dated Nov. 21, 2017 issued in PCT/JP2017/036424.

*Primary Examiner* — Peet Dhillon
(74) *Attorney, Agent, or Firm* — Scully, Scott, Murphy & Presser, P.C.

(57) ABSTRACT

An endoscope system includes: a capsule endoscope that is capable of being introduced into a subject and that wirelessly transmits image data obtained by capturing an image inside the subject; a plurality of receiving devices each of which receives and records the image data wirelessly transmitted by the capsule endoscope, each of the receiving devices including a receiver configured to receive, by using wireless communication, identification information for identifying the capsule endoscope, a recorder configured to record the image data, and a first controller configured to establish wireless communication with the capsule endoscope according to a reception result of the receiver and record, in the recorder, the image data transmitted from the capsule endoscope by associating the image data with the identification information of the capsule endoscope; and a workstation that is connected to the plurality of the receiving devices, the workstation including a processor comprising hardware.

9 Claims, 12 Drawing Sheets

(51) Int. Cl.
*H04W 76/10* (2018.01)
*A61B 1/00* (2006.01)
*H04N 5/77* (2006.01)
*H04B 1/06* (2006.01)
*H04B 1/38* (2015.01)

(52) U.S. Cl.
CPC ........ *A61B 1/0005* (2013.01); *A61B 1/00016* (2013.01); *A61B 1/00059* (2013.01); *A61B 1/041* (2013.01); *H04N 5/77* (2013.01); *H04N 7/183* (2013.01); *H04W 76/10* (2018.02); *H04B 1/06* (2013.01); *H04B 1/38* (2013.01)

(56) References Cited

U.S. PATENT DOCUMENTS

2014/0336454 A1\* 11/2014 Taniguchi ............ A61B 1/0002
600/103
2015/0031954 A1\* 1/2015 Kimoto .............. A61B 1/00006
600/118

FOREIGN PATENT DOCUMENTS

JP 2008-301953 A 12/2008
WO WO 2014/069608 A1 5/2014

\* cited by examiner

FIG.5

| CAPSULE ID |
|---|
| 11111111 |
| 22222222 |
| 33333333 |
| ⋮ |
| XXXXXXXX |

| CAPSULE ID |
|---|
| 11111111 |

FIG.7

| PATIENT ID |
|---|
| 00001 |

FIG.8

| PATIENT ID | CAPSULE ID | IMAGE DATA |
|---|---|---|
| 00001 | 11111111 | 111 |

FIG.10

| PATIENT ID | CAPSULE ID |
|---|---|
| 00001 | 11111111 |

| PATIENT ID | CAPSULE ID | STATUS |
|---|---|---|
| 00001 | 11111111 | TEMPORARY |
| 00002 | 22222222 | TEMPORARY |
| 00003 | 33333333 | TEMPORARY |
| 00004 | 44444444 | TEMPORARY |
| 00005 | 55555555 | TEMPORARY |

| PATIENT ID | CAPSULE ID | STATUS |
|---|---|---|
| 00001 | 11111111 | OFFICIAL |
| 00002 | 22222222 | TEMPORARY |
| 00003 | 33333333 | TEMPORARY |
| 00004 | 44444444 | TEMPORARY |
| 00005 | 55555555 | TEMPORARY |

FIG.15

| PATIENT ID | CAPSULE ID | STATUS |
|---|---|---|
| 00002 | 22222222 | TEMPORARY |
| 00003 | 33333333 | TEMPORARY |
| 00004 | 44444444 | TEMPORARY |
| 00005 | 55555555 | TEMPORARY |

| PATIENT ID | CAPSULE ID | STATUS |
|---|---|---|
| 00001 | 11111111 | OFFICIAL |

ENDOSCOPE SYSTEM, RECEIVING DEVICE, WORKSTATION, SETTING METHOD, AND COMPUTER READABLE RECORDING MEDIUM

CROSS-REFERENCE TO RELATED APPLICATION

This application is a continuation of PCT International Application No. PCT/JP2017/036424 filed on Oct. 6, 2017 which claims the benefit of priority from Japanese Patent Application No. 2016-237604, filed on Dec. 7, 2016, the entire contents of which are incorporated herein by reference.

BACKGROUND

The present disclosure relates to an endoscope system, a receiving device, a workstation, a setting method, and a computer recording medium.

In the field of endoscopy, there is a known examination performed by using a capsule endoscope that is introduced into a subject and captures images inside the subject. The capsule endoscope is a device having an image capturing function, a wireless transmission function, and the like inside a capsule shaped casing that is formed with a size so as to be capable of being introduced into the digestive tract of the subject. The capsule endoscope swallowed from the mouth of the subject performs imaging while moving inside the digestive tract by a peristaltic movement and generates image data. The generated pieces of image data are sequentially and wirelessly transmitted outside the subject from the capsule endoscope.

The image data wirelessly transmitted from the capsule endoscope is received by a receiving device provided outside the subject and is then recorded in a built-in memory that is built in the receiving device or recorded in a recording medium, such as a portable memory, that may be freely inserted and removed. After the end of examination, the image data recorded in the recording medium is transferred to a workstation and is subjected to predetermined image processing (for example, see Japanese Laid-open Patent Publication No. 2008-301953). A healthcare professional diagnoses the subject by observing images associated with image data that has been subjected to image processing.

SUMMARY

There is a need for an endoscope system, a receiving device, a workstation, a setting method, and a program capable of efficiently perform the initialization process even when one of a plurality of receiving devices is used.

An endoscope system according to one aspect of the present disclosure includes: a capsule endoscope that is capable of being introduced into a subject and that wirelessly transmits image data obtained by capturing an image inside the subject; a plurality of receiving devices each of which receives and records the image data wirelessly transmitted by the capsule endoscope, each of the receiving devices including a receiver configured to receive, by using wireless communication, identification information for identifying the capsule endoscope, a recorder configured to record the image data, and a first controller configured to establish wireless communication with the capsule endoscope according to a reception result of the receiver and record, in the recorder, the image data transmitted from the capsule endoscope by associating the image data with the identification information of the capsule endoscope; and a workstation that is connected to the plurality of the receiving devices, the workstation including a processor comprising hardware, the processor being configured to execute acquiring, from a recording medium that records the identification information attached to the capsule endoscope, the identification information and subject identification information for identifying the subject, searching for the receiving device that has recorded the same identification information as the acquired identification information, and performing, on the receiving device specified according to a search result obtained by the searching, an initialization process for associating the subject identification information with the image data.

A receiving device according to another aspect of the present disclosure for being connected to a workstation so as to perform communication with the workstation and for receiving and recording image data wirelessly transmitted from a capsule endoscope that wirelessly transmits image data obtained by capturing an image inside the subject, includes: a receiver configured to receive, by using wireless communication, identification information for identifying the capsule endoscope; a recorder configured to record the image data; a first transceiver configured to receive information from the workstation and receive subject identification information for identifying the subject from the workstation; and a first controller configured to establish wireless communication with the capsule endoscope according to a reception result of the receiver and record, in the recorder, the image data transmitted from the capsule endoscope by associating the image data with the identification information of the capsule endoscope, wherein when the first controller receives the subject identification information from the workstation via the first transceiver, the first control unit records, in the recorder, the image data, the identification information, and the subject identification information in an associated manner.

A workstation according to still another aspect of the present invention, to which a plurality of receiving devices each of which receives and records image data wirelessly transmitted from a capsule endoscope is connected so as to perform communication, includes: a processor comprising hardware, the processor being configured to execute acquiring, from a recording medium that records identification information attached to the capsule endoscope, the identification information and subject identification information for identifying the subject; searching for the receiving device that has recorded the same identification information as the acquired identification information; and performing, on the receiving device specified according to a search result obtained by the searching, an initialization process for associating the subject identification information with the image data.

The above and other features, advantages and technical and industrial significance of this invention will be better understood by reading the following detailed description of presently preferred embodiments of the disclosure, when considered in connection with the accompanying drawings.

BRIEF DESCRIPTION OF THE DRAWINGS

FIG. 5 is a diagram schematically illustrating a table of capsule IDs of the capsule endoscope displayed by the receiving device according to the first embodiment.

FIG. 6 is a diagram schematically illustrating an example of a capsule ID of the capsule endoscope according to the first embodiment.

FIG. 7 is a diagram schematically illustrating an example of a patient ID according to the first embodiment.

FIG. 8 is a diagram schematically illustrating an association relationship of the patient ID, the capsule ID, and the image data according to the first embodiment.

FIG. 10 is a diagram schematically illustrating an association relationship between a patient ID and a capsule ID according to the second embodiment.

FIG. 13 is a diagram schematically illustrating a table of temporary initialization information displayed by a receiving device according to the third embodiment.

FIG. 14 is a diagram schematically illustrating a table of information displayed by the receiving device according to the third embodiment.

FIG. 15 is a diagram schematically illustrating a table of information displayed by another receiving device according to the third embodiment.

FIG. 16 is a diagram schematically illustrating another piece of information displayed by the receiving device according to the third embodiment.

DETAILED DESCRIPTION

Figure 1:
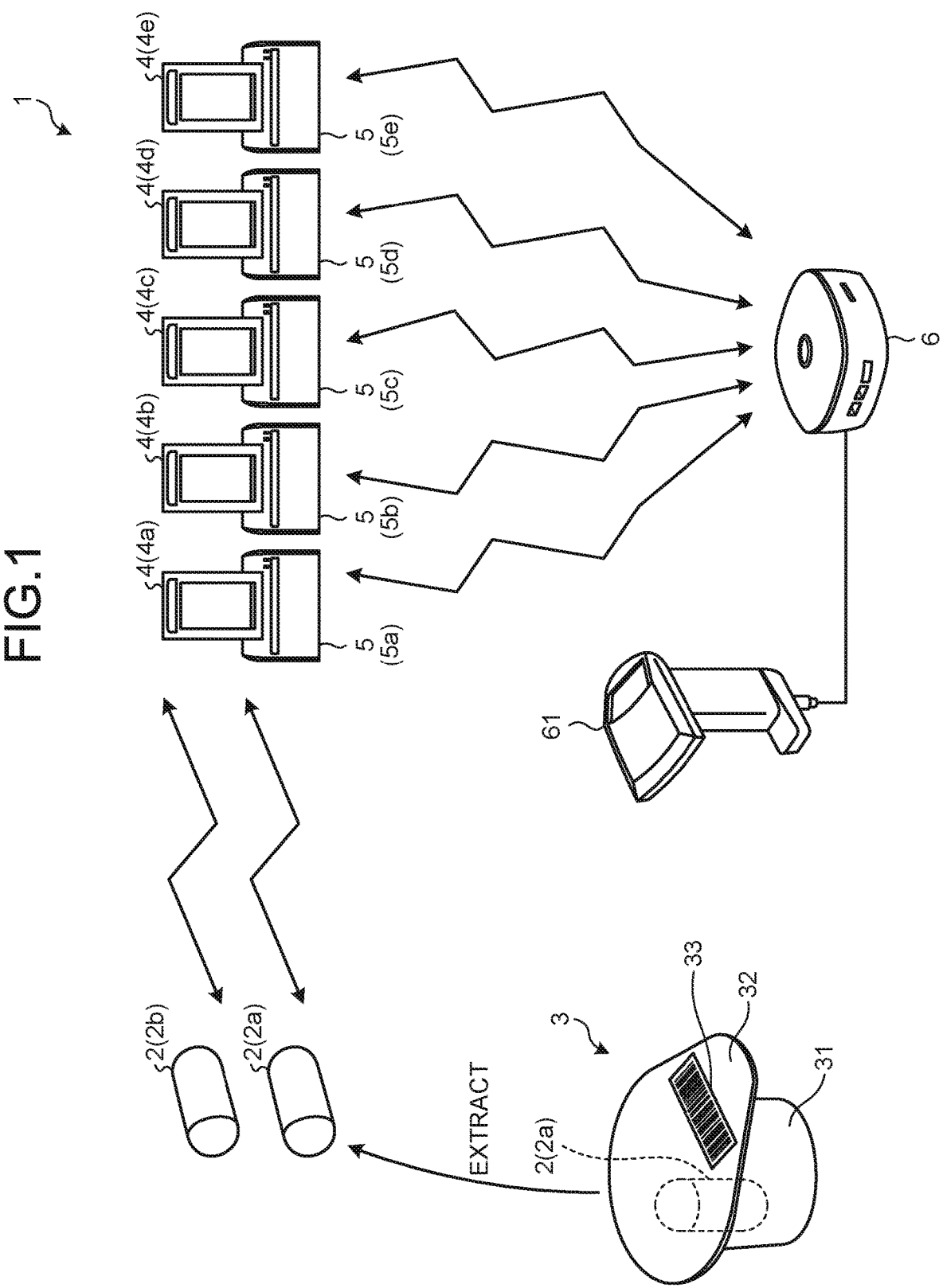
FIG. 1 is a schematic diagram illustrating, in outline, a configuration of an endoscope system according to a first embodiment.

In the following, an endoscope system provided with a capsule endoscope will be explained with reference to accompanying drawings as an example of an endoscope system according to an embodiment. Furthermore, in a description below, a capsule endoscope that is orally introduced into a subject and that performs imaging will be described as an example; however, the present disclosure is not limited to the embodiment. Namely, the present disclosure may also be applied to various capsule endoscopes, such as a capsule endoscope that is orally swallowed with, for example, a physiological saline solution or water by the subject and that captures images inside the body cavity of the subject. Furthermore, in the drawings used for the following description, shapes, sizes, and positional relationships are only schematically illustrated so that the content of the present disclosure may be understood. Thus, the present disclosure is not limited to only the shapes, the sizes, and the positional relationships exemplified in the drawings. Furthermore, the same reference signs are used to designate the same elements throughout the drawings.

First Embodiment

Configuration of Endoscope System

FIG. 1 is a schematic diagram illustrating, in outline, a configuration of an endoscope system according to a first embodiment. An endoscope system 1 illustrated in FIG. 1 includes a capsule endoscope 2 that is introduced into a subject, that captures in-vivo images inside the subject, and that wirelessly transmits the captured images; an accommodating case 3 that is capable of accommodating the capsule endoscope 2; a plurality of receiving devices 4a to 4e each of which receives and records a radio signal including image data received from the capsule endoscope 2 via a receiving antenna (not illustrated); cradles 5a to 5e to which the receiving devices 4a to 4e are connected, respectively, and that charge the receiving devices 4a to 4e, respectively; and a workstation 6 that is connected to each of the plurality of the receiving devices 4a to 4e, that acquires image data recorded in each of the plurality of the receiving devices 4a to 4e, and that transmits examination information or the like to each of the plurality of the receiving devices 4a to 4e.

The capsule endoscope 2 has an image capturing function for capturing images inside the subject and a wireless communication function for wirelessly transmitting a radio signal including identification information (hereinafter, referred to as a "capsule ID") for identifying the image data obtained by capturing inside the subject and identifying the capsule endoscope 2. The capsule endoscope 2 passes an esophagus inside the subject by being swallowed from the mouth of the subject and moves inside the body cavity of the subject by a peristaltic movement of a lumen of a digestive tract. The capsule endoscope 2 sequentially captures images inside the body cavity of the subject at minute time intervals of, for example 0.5 seconds (2 fps) while moving inside the body cavity of the subject, generates image data of the captured image inside the subject, and sequentially and wirelessly transmits the pieces of image data. Furthermore, a configuration of the capsule endoscope 2 will be described in detail later.

The accommodating case 3 accommodates the capsule endoscope 2 in which an interior portion has been sterilized. The accommodating case 3 includes a blister pack 31 that accommodates therein the capsule endoscope 2; a sterile sheet 32 that blocks an opening of the blister pack 31; and an identification information recording unit 33 that is provided on an upper surface of the sterile sheet 32 and in which the capsule ID of the capsule endoscope 2 accommodated in the blister pack 31 has been recorded. The identification information recording unit 33 is implemented by using, for example, a bar code, a matrix-type two-dimensional code including a two-dimensional code or a QR code (registered trademark), an IC chip, and the like. Furthermore, the identification information recording unit 33 may also be implemented by using an integrated Circuit (IC) chip or the like that transmits a capsule ID in accordance with a predetermined wireless communication standard. Furthermore, in the first embodiment, a description will be given with the assumption that the identification information recording unit 33 is a bar code.

A receiving device 4 records image data or display an image associated with the image data on the subject included in the radio signal received from the capsule endoscope 2 via a plurality of receiving antenna (not illustrated) that is freely attached and removed. The receiving device 4 records or displays the capsule ID that is used to identify the capsule endoscope 2 included in the radio signal. The receiving device 4 is carried by the subject by being stored in a receiving device holder (not illustrated) during the period of time for which an examination using the capsule endoscope 2 is being performed, such as the period of time for which, for example, the capsule endoscope 2 is introduced from the mouth of the subject, moves inside the digestive tract, and is discharged from inside the subject. After the end of the examination performed by using the capsule endoscope 2, the receiving device 4 is removed from the subject and is charged by being connected to a cradle 5. The receiving device 4 is connected to the workstation 6 by using a wireless connection in order to transfer the image data or the like received from the capsule endoscope 2. A configuration of the receiving device 4 will be described in detail later.

The workstation 6 is implemented by using a personal computer that does not have a display monitor. The workstation 6 performs predetermined image processing on the image data of the subject transferred from the receiving device 4; associates the image data, the capsule ID of the capsule endoscope 2, and subject identification information (hereinafter, referred to as a "patient ID") on the subject, a patient, or the like; and records the associated information. The workstation 6 transmits, via a network, the image data to a personal computer, a mobile terminal device, or the like that performs observation. Furthermore, a portable memory card or the like may also be connected to the workstation 6 so as to be freely attached to and removed from the workstation 6 and, then, the image data, the capsule IDs, and the patient IDs may also be associated with each other and recorded in this memory card. Furthermore, the workstation 6 includes an acquiring unit 61 that acquires the capsule ID of the capsule endoscope 2 from the identification information recording unit 33 included in the accommodating case 3. A configuration of the workstation 6 will be described in detail later.

Configuration of Capsule Endoscope

Figure 2:
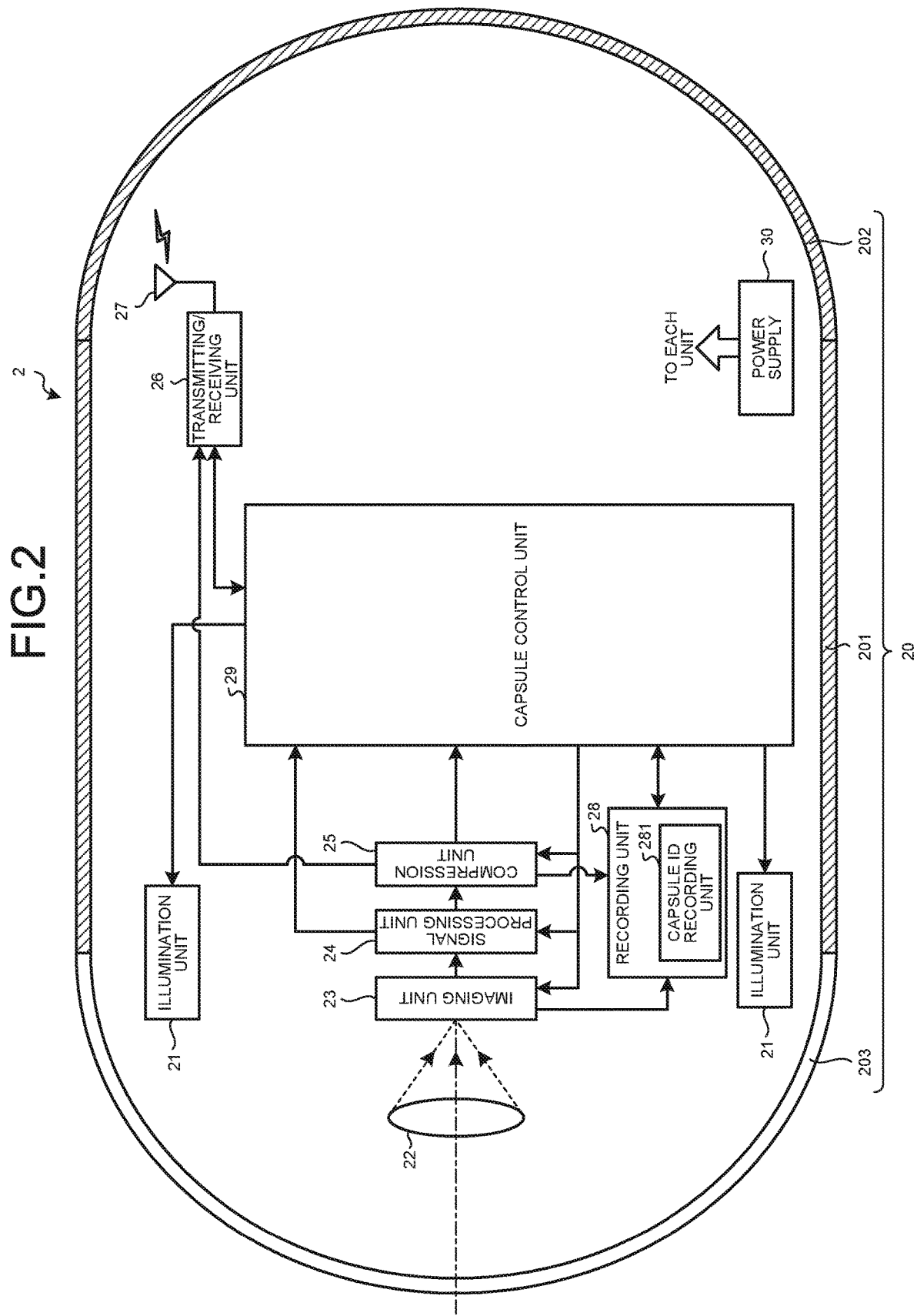
FIG. 2 is a block diagram illustrating a functional configuration of a capsule endoscope according to the first embodiment.

In the following, a configuration of the capsule endoscope 2 will be described. FIG. 2 is a block diagram illustrating a functional configuration of the capsule endoscope 2.

The capsule endoscope 2 illustrated in FIG. 2 includes a capsule-shaped casing 20, an illumination unit 21, an optical system 22, an imaging unit 23, a signal processing unit 24, a compression unit 25, a transmitting/receiving unit 26, a recording unit 28, a capsule control unit 29, and a power supply 30.

The capsule-shaped casing 20 is an outer casing formed with a size and a shape so as to be capable of being introduced in an interior of an organ of the subject and is implemented by covering both ends of the openings of a cylindrical casing 201 by dome-shaped casings 202 and 203. The dome-shaped casing 203 is formed by using a transparent member that may pass illumination light radiated by the illumination unit 21. The capsule-shaped casing 20 formed by the cylindrical casing 201 and the dome-shaped casings 202 and 203 includes therein, as illustrated in FIG. 2, the illumination unit 21, the optical system 22, the imaging unit 23, the signal processing unit 24, the compression unit 25, the transmitting/receiving unit 26, an antenna 27, the recording unit 28, the capsule control unit 29, and the power supply 30.

The illumination unit 21 radiates, under the control of the capsule control unit 29, illumination light, such as white light or the like, toward an area including at least the field of view of imaging of the capsule endoscope 2 through the dome-shaped casing 203. The illumination unit 21 is constituted by using a light emitting diode (LED) or the like.

The optical system 22 condenses light reflected from a mucous membrane of the subject onto the imaging surface of the imaging unit 23 and forms an object image. The optical system 22 is formed by using one or more lenses, such as condenser lenses or focus lenses.

The imaging unit 23 sequentially generates, under the control of the capsule control unit 29, the image signal of the object image formed by the optical system 22 in accordance with a predetermined frame rate and outputs the generated image signal to each of the signal processing unit 24 and the recording unit 28. The imaging unit 23 is formed by using an imaging sensor, such as a complementary metal oxide semiconductor (CMOS), a charge coupled device (CCD), or the like.

The signal processing unit 24 performs, under the control of the capsule control unit 29, predetermined signal processing on the image signal that has been input from the imaging unit 23, generates image data, and outputs the image data to the compression unit 25 and the capsule control unit 29. The predetermined signal processing mentioned here is a gain adjustment process, an A/D conversion process, or the like to be performed on the image signal. Furthermore, the signal processing unit 24 is formed by using an IC, large scale integration (LSI), an application specific integrated circuit (ASIC), or the like.

The compression unit 25 generates, under the control of the capsule control unit 29, compression image data by compressing the image data that has been input from the signal processing unit 24 in accordance with a predetermined compression process and then outputs the compressed image data to the transmitting/receiving unit 26, the recording unit 28, and the capsule control unit 29. Here, examples of the predetermined compression process include a compression process performed by calculating a difference between pixel values for each of the adjacent pixels and assigning a code having a smaller value to the difference that is closer to zero, a compression process performing frequency conversion on the image data and assigning a code having a smaller value to a lower frequency signal, and the like.

The transmitting/receiving unit 26 sequentially and wirelessly transmits the image data input from the compression unit 25 to the outside via the antenna 27. Specifically, the transmitting/receiving unit 26 generates a radio signal by performing signal processing, such as modulation, on the image data that has been input from the compression unit 25 and then transmits the generated radio signal to the outside. Furthermore, the transmitting/receiving unit 26 receives the radio signal transmitted from the outside via the antenna 27, performs a demodulation process or the like on the received radio signal, and outputs the processed radio signal to the capsule control unit 29. Furthermore, the transmitting/receiving unit 26 transmits the identification information that is used to identify the capsule endoscope 2 recorded by the recording unit 28, which will be described later, to the outside via the antenna 27.

The recording unit 28 is constituted by using a read only memory (ROM), a random access memory (RAM), and the like and records various kinds of programs executed by the capsule endoscope 2, the image data, and various kinds of information that is being processed by the capsule endoscope 2. Furthermore, the recording unit 28 includes a capsule ID recording unit 281 that records the capsule ID that is used to identify the capsule endoscope 2.

The capsule control unit 29 is constituted by using a central processing unit (CPU) or the like, performs control of driving each component included in the capsule endoscope 2, and performs control of input/output of the signal between each of the components.

The power supply 30 is constituted by using a storage battery, such as a button type battery or a capacitor, and a switch that is switched by a command received from the capsule control unit 29. The power supply 30 supplies an electrical power supply to each of the components in the capsule endoscope 2.

Configuration of Receiving Device and Workstation

Figure 3:
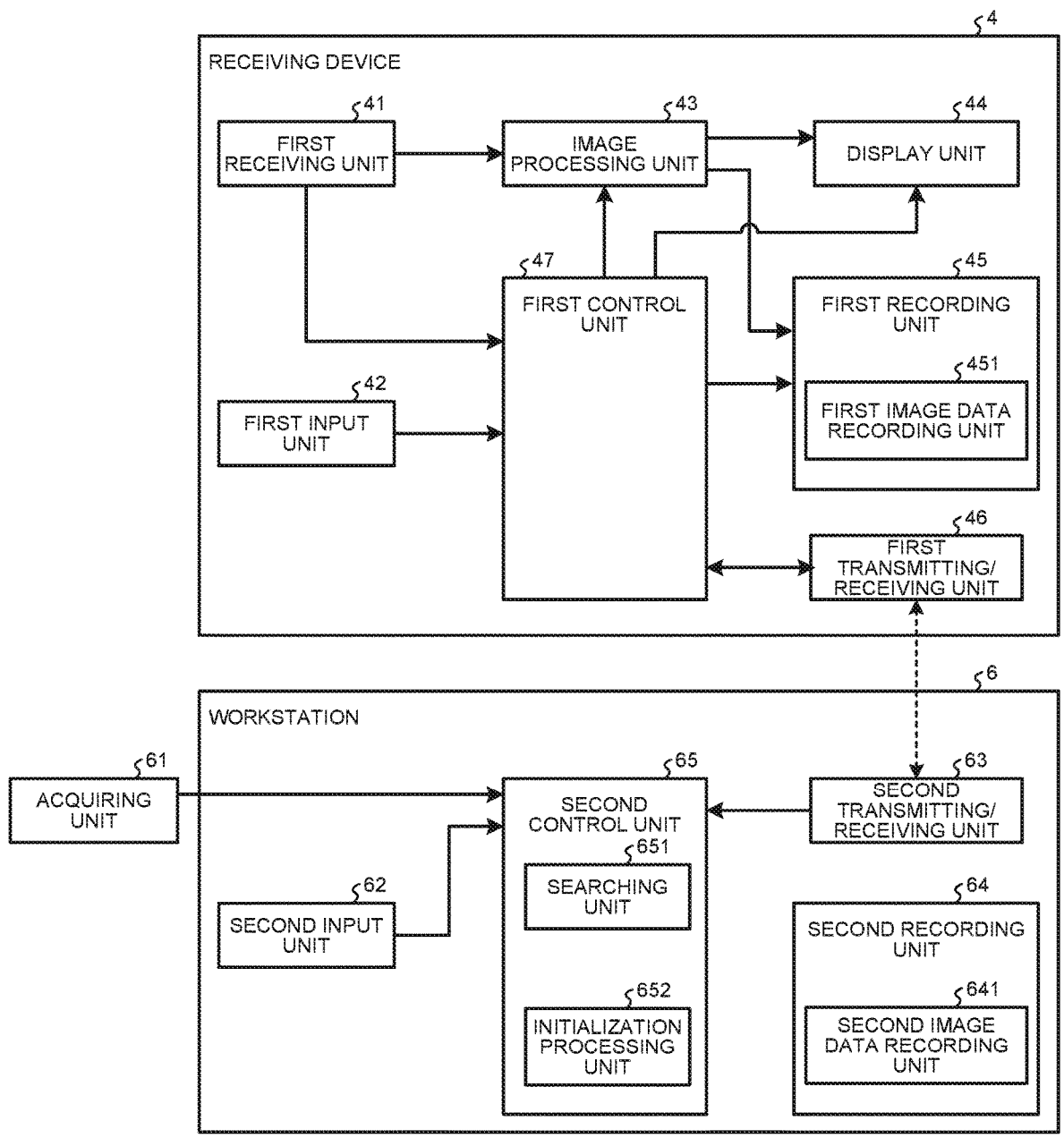
FIG. 3 is a block diagram illustrating a functional configuration of a receiving device and a workstation according to the first embodiment.

In the following, a configuration of each of the receiving device 4 and the workstation 6 will be described. FIG. 3 is a block diagram illustrating a functional configuration of each of the receiving device 4 and the workstation 6. Furthermore, in FIG. 3, after the configuration of the receiving device 4 has been described the configuration of the workstation 6 will be described.

Configuration of Receiving device

First, the configuration of the receiving device 4 will be described.

As illustrated in FIG. 3, the receiving device 4 includes a first receiving unit 41, a first input unit 42, an image processing unit 43, a display unit 44, a first recording unit 45, a first transmitting/receiving unit 46, and a first control unit 47.

The first receiving unit 41 receives the radio signal transmitted from the capsule endoscope 2 via a plurality of antennas (not illustrated) and then outputs the radio signal to the image processing unit 43 and the first control unit 47. The first receiving unit 41 performs demodulation process on the radio signal and outputs the processed radio signal to the image processing unit 43.

The first input unit 42 receives an input of various operations related to the receiving device 4 and outputs the content of the received various operations to the first control unit 47. The first input unit 42 is constituted by using, for example, a switch, a button, or the like.

The image processing unit 43 performs, under the control of the first control unit 47, predetermined image processing on the image data included in the radio signal input form the first receiving unit 41 and then outputs the processed image data to the display unit 44 or the first recording unit 45. Here, examples of the predetermined image processing include, for example, a demosaicing process, a white balance adjustment process, and the like.

The display unit 44 displays, under the control of the first control unit 47, the image associated with the image data input from the image processing unit 43 or various kinds of information related to the receiving device 4. The display unit 44 is constituted by using a display panel, such as a liquid crystal or organic electro luminescence (EL) display panel. Furthermore, the display unit 44 displays, under the control of the first control unit 47, the table of capsule IDs of the plurality of the capsule endoscope 2 (for example, a capsule endoscopes 2a and 2b illustrated in FIG. 1) received by the first receiving unit 41.

The first recording unit 45 records programs for operating the receiving device 4 and various kinds of information related to the receiving device 4. The first recording unit 45 is constituted by using a RAM, a ROM, and the like. Furthermore, the first recording unit 45 includes a first image data recording unit 451 that records image data. Furthermore, the first recording unit 45 may also be constituted by using a memory card or the like that is freely attached and removed from outside the receiving device 4.

The first transmitting/receiving unit 46 transmits, under the control of the first control unit 47, the image data to the workstation 6 in accordance with a predetermined communication standard. The first transmitting/receiving unit 46 transmits various kinds of data by using one of the communication modes from among a Wireless Fidelity (Wi-Fi) (registered trademark) communication, a Bluetooth (registered trademark) communication mode, a communication mode using 4G or 3G radio bands, a Worldwide Interoperability for Microwave Access (WiMAX) communication mode, and the like.

Furthermore, in addition to wireless transmission, the first transmitting/receiving unit 46 may also transmit various kinds of data to the workstation 6 in a wired manner.

The first control unit 47 controls each of the units in the receiving device 4. The first control unit 47 is constituted by using a CPU, a field programmable gate array (FPGA), or the like. The first control unit 47 establishes wireless communication with the capsule endoscope 2 according to a reception result of the first receiving unit 41, associates the image data transmitted from the capsule endoscope 2 with the capsule ID of the capsule endoscope 2, and records the associated information in the first image data recording unit 451.

Configuration of Workstation

In the following, a configuration of the workstation 6 will be described.

As illustrated in FIG. 3, the workstation 6 includes an acquiring unit 61, a second input unit 62, a second transmitting/receiving unit 63, a second recording unit 64, and a second control unit 65.

The acquiring unit 61 acquires the capsule ID of the capsule endoscope 2 and outputs the acquired capsule ID to the second control unit 65. Specifically, the acquiring unit 61 reads the capsule ID (identification code) of the capsule endoscope 2 from the identification information recording unit 33 provided on the upper surface of the sterile sheet 32 in the accommodating case 3 and outputs the capsule ID to the second control unit 65. The acquiring unit 61 is constituted by using a bar code reader; a digital camera having an image capturing function capable of acquiring, for example, a QR code (registered trademark), or the like; a magnetic reader capable of acquiring magnetic information; or the like. Furthermore, the acquiring unit 61 is connected to the workstation 6 in a wired manner so as to be freely attached and removed. Of course, the acquiring unit 61 may also be wirelessly connected to the workstation 6 in accordance with the predetermined communication standard.

The second input unit 62 receives an input of various operations related to the workstation 6 and outputs the content of the received input operations to the second control unit 65. The second input unit 62 is constituted by using a keyboard, a mouse, or the like that is freely attached to and removed from, for example, the workstation 6.

The second transmitting/receiving unit 63 receives, under the control of the second control unit 65, the image data from the receiving device 4 in accordance with the predetermined communication standard, outputs the received image data to the second control unit 65, and transmits the patient ID for identifying a subject or a patient to the receiving device 4. Furthermore, in the first embodiment, communication is performed, in a two-way direction, with one of the receiving device 4, an external personal computer, and a mobile terminal by using Wi-Fi communication.

The second recording unit 64 records programs for operating the workstation 6 and various kinds of information related to the workstation 6. The second recording unit 64 is constituted by using a RAM, a ROM, or the like. Furthermore, the second recording unit 64 includes a second image data recording unit 641 that records image data. Furthermore, the second recording unit 64 may also be constituted by using a memory card or the like that is freely attached and removed from outside the workstation 6.

The second control unit 65 controls an operation of each of the units included in the workstation 6. The second control unit 65 is constituted by using a CPU or the like. The second control unit 65 includes a searching unit 651 and an initialization processing unit 652.

The searching unit 651 searches for the receiving device 4 that records the same capsule ID as that acquired by the acquiring unit 61. Specifically, the searching unit 651 searches, based on the capsule ID acquired by the acquiring unit 61, for the receiving device 4, from among the receiving devices 4a to 4e, that has established wireless communication with the capsule endoscope 2a. For example, if the capsule endoscope 2a and the receiving device 4a have established wireless communication, the searching unit 651 searches for the receiving device 4a, from among the receiving devices 4a to 4e, by recognizing that the receiving device 4a has recorded the same capsule ID as that acquired by the acquiring unit 61.

The initialization processing unit 652 performs, on the receiving device 4 specified according to the search result obtained by the searching unit 651, an initialization process for associating the patient ID of the subject with the image data. Here, the patient ID is identification information for identifying at least a patient, such as age, gender, examination content, and the number of examinations.

Process performed by Endoscope System

Figure 4:
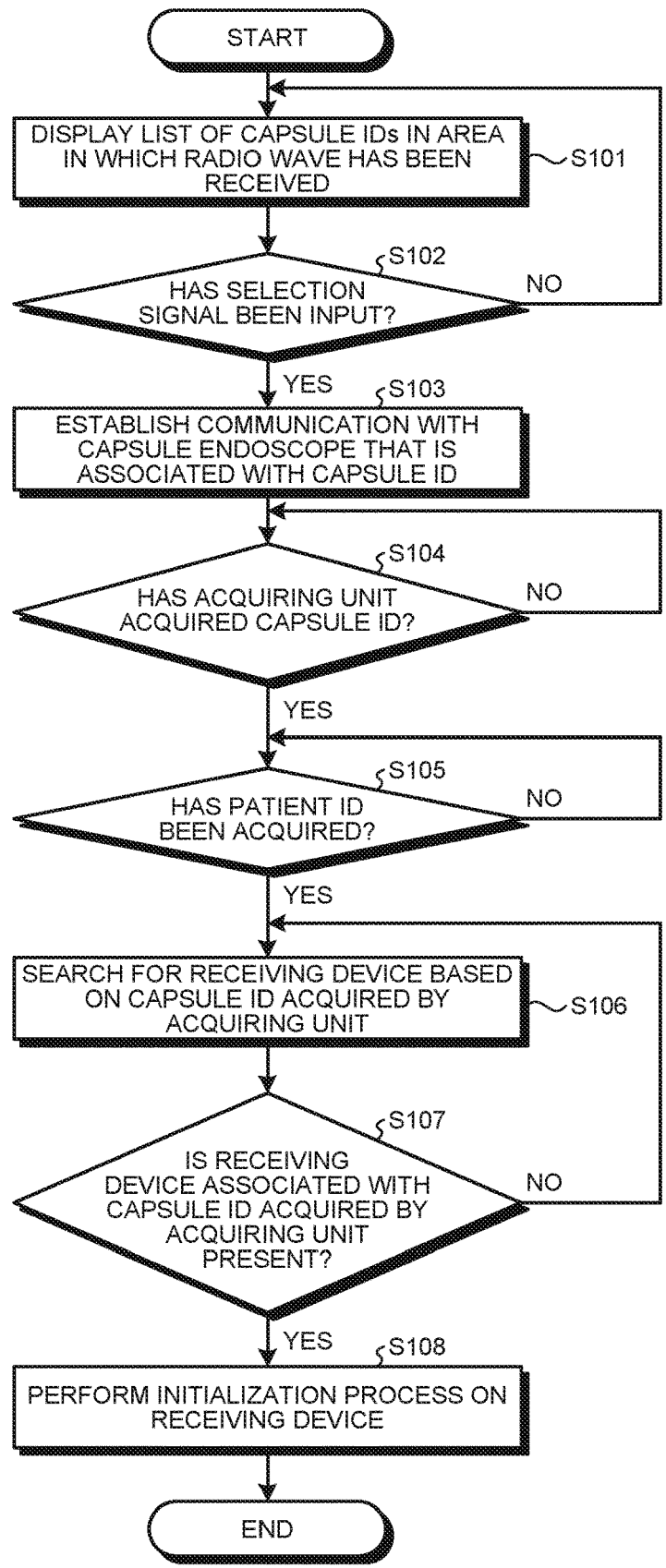
FIG. 4 is a flowchart illustrating an outline of a process performed by the endoscope system according to the first embodiment.

In the following, the process performed by the endoscope system 1 will be described. FIG. 4 is a flowchart illustrating an outline of the process performed by the endoscope system 1. Furthermore, in FIG. 4, a description will be given of a case in which the number of the capsule endoscopes 2 is two (the capsule endoscopes 2a and 2b illustrated in FIG. 1) and, furthermore, the number of the receiving device 4 is five (the receiving devices 4a to 4e illustrated in FIG. 1). Furthermore, in FIG. 4, a description will be given of a state in a case where a user uses the receiving device 4a out of the receiving devices 4a to 4e and the capsule endoscope 2a. Furthermore, in general, if the user actually uses one of the receiving devices 4a to 4e, the user selects the one that has already been charged.

As illustrated in FIG. 4, first, the receiving device 4a displays the table of capsule IDs (identification) located in the vicinity of an area in which a radio wave has been received (Step S101). Specifically, the receiving device 4a receives the radio wave that indicates the capsule ID sent out from each of the capsule endoscopes 2a and 2b and displays the table of the received capsule IDs on the display unit 44. For example, as illustrated in FIG. 5, the receiving device 4a displays a table T1 of the received capsule IDs on the display unit 44. Consequently, a user may intuitively grasp the table of the capsule endoscopes 2 capable of performing communication establishment (pairing) with the receiving device 4a.

Subsequently, if a selection signal for selecting the capsule endoscope 2 (for example, the capsule endoscope 2a) that establishes communication with the receiving device 4a from the table of capsule IDs displayed by the display unit 44 is input from the first input unit 42 (Yes at Step S102), communication is established with the capsule endoscope 2 that is associated with the capsule ID (Step S103). Specifically, the first control unit 47 performs a communication establishment process for establishing wireless communication with the capsule endoscope 2a, associating the image data transmitted from the capsule endoscope 2a with the capsule ID of the capsule endoscope 2a, and recording the associated information in the first image data recording unit 451. Consequently, the image data transmitted from the capsule endoscope 2a is recorded in the first image data recording unit 451, in association with the capsule ID of the capsule endoscope 2a.

At Step S102, if a selection signal for selecting the capsule endoscope 2 that performs communication establishment with the receiving device 4a from the table of capsule IDs displayed by the display unit 44 is not input from the first input unit 42 (No at Step S102), the receiving device 4a returns to Step S101.

At Step S104, the second control unit 65 determines whether the acquiring unit 61 has acquired the capsule ID. Specifically, the second control unit 65 determines whether the acquiring unit 61 has acquired the capsule ID of the capsule endoscope 2a from the identification information recording unit 33 that is provided on the upper surface of the sterile sheet 32 of the accommodating case 3. For example, as illustrated in FIG. 6, the second control unit 65 determines whether the acquiring unit 61 has acquired the capsule ID (11111111) of the capsule endoscope 2a from the identification information recording unit 33 provided on the upper surface of the sterile sheet 32 of the accommodating case 3. If it is determined, by the second control unit 65, that the acquiring unit 61 has acquired the capsule ID (Yes at Step S104), the endoscope system 1 moves to Step S105, which will be described later. In contrast, if it is determined, by the second control unit 65, that the acquiring unit 61 has not acquired the capsule ID (No at Step S104), the second control unit 65 continues this determination.

At Step S105, the second control unit 65 determines whether the acquiring unit 61 has acquired a patient ID. Specifically, the second control unit 65 determines whether a user has read the patient ID attached to the subject by using the acquiring unit 61. For example, as illustrated in FIG. 7, the second control unit 65 determines whether the user has read the patient ID (00001) attached to the subject by using the acquiring unit 61. Furthermore, the second control unit 65 determines whether the user has read the patient ID by using the acquiring unit 61; however, there is no need to read the patient ID and it may also determine whether, for example, the patient ID has been recorded in the second recording unit 64. In this case, the user may input the patient ID via the second input unit 62. Of course, the user may input the patient ID to the workstation 6 by using a personal computer provided with a display monitor arranged in another room. If it is determined, by the second control unit 65, that the acquiring unit 61 has acquired the patient ID (Yes at Step S105), the endoscope system 1 moves to Step S106, which will be described later. In contrast, if it is determined, by the second control unit 65, that the acquiring unit 61 has not acquired the patient ID (No at Step S105), the second control unit 65 continues this determination.

At Step S106, the searching unit 651 searches for, based on the capsule ID acquired by the acquiring unit 61, the receiving device 4a, from among the plurality of the receiving devices 4a to 4e connected to the workstation 6, in which the same capsule ID as that acquired by the acquiring unit 61 has been recorded.

Subsequently, if it is determined, by the searching unit 651, that the receiving device 4a associated with the capsule ID acquired by the acquiring unit 61 is present (Yes at Step S107), the initialization processing unit 652 performs the initialization process on the receiving device 4a (Step S108). Specifically, as illustrated in FIG. 8, the initialization processing unit 652 performs the initialization process, on the receiving device 4a, for associating the patient ID (00001), the capsule ID (11111111), and the image data (111). In this case, the initialization processing unit 652 may also associate the patient ID, the capsule ID, and the image data. Consequently, because the initialization process is automatically performed on the receiving device 4a, it is possible to efficiently perform the initialization process on the plurality of the receiving devices 4a to 4e without performing a complicated operation. After Step S108, the endoscope system 1 ends the process.

At Step S107, if it is determined, by the searching unit 651, that the receiving device 4a associated with the capsule ID acquired by the acquiring unit 61 is not present (No at Step S107), the workstation 6 returns to Step S106.

According to the first embodiment described above, it is possible to efficiently perform the initialization process even when one of the plurality of the receiving devices 4a to 4e is used.

Second Embodiment

In the following, a second embodiment will be described. The second embodiment has the same configuration as that described in the first embodiment but a process to be performed is different from that described in the first embodiment. Specifically, in the first embodiment described above, an examination of the subject is started after having performed the initialization process on the receiving device; however, in the second embodiment, after having performed the examination of the subject, a process for associating the capsule ID, which has been associated with the patient ID recorded in the workstation, with the capsule ID, which has been recorded in the receiving device, is performed. In a description below, the process performed by an endoscope system according to the second embodiment will be described. Furthermore, components that are identical to those in the endoscope system 1 according to the first embodiment are assigned the same reference numerals and descriptions thereof will be omitted.

Process performed by Endoscope System

Figure 9:
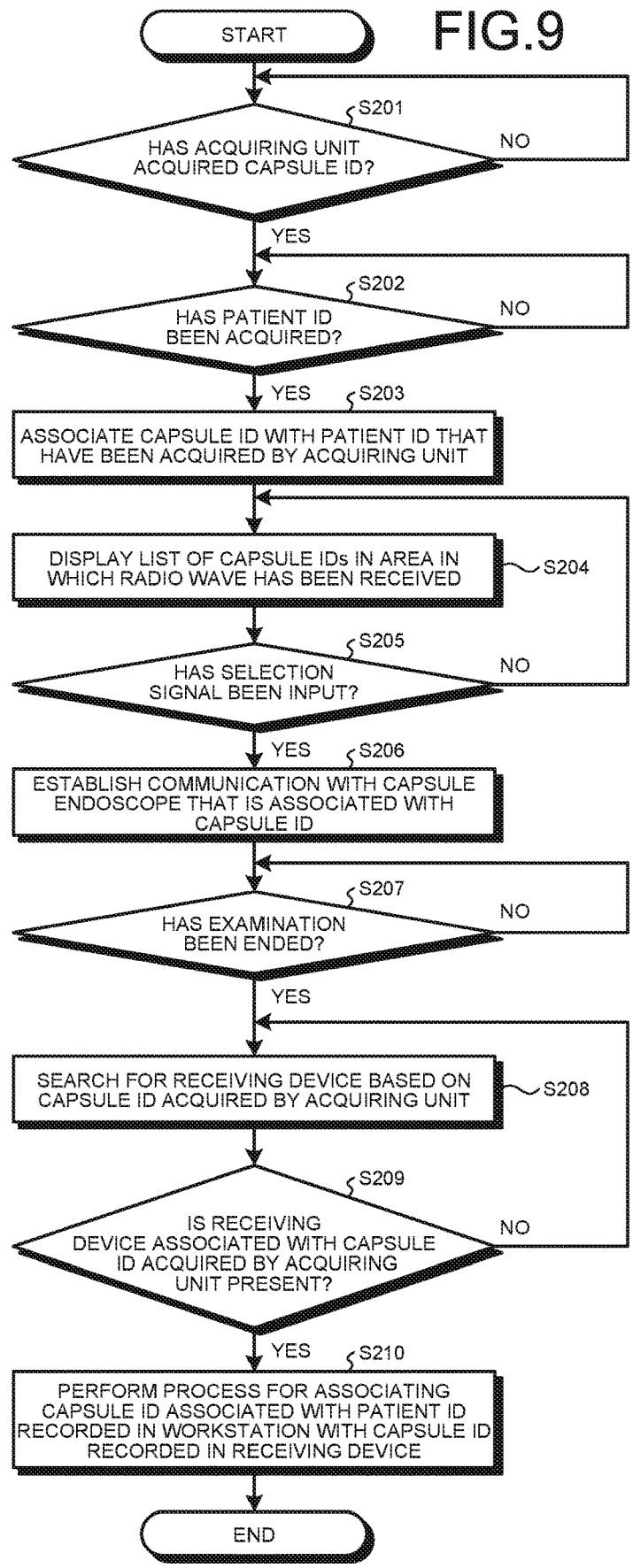
FIG. 9 is a flowchart illustrating an outline of a process performed by an endoscope system according to a second embodiment.

FIG. 9 is a flowchart illustrating an outline of a process performed by the endoscope system 1 according to a second embodiment. Furthermore, in FIG. 9, a description will be given of a case in which the number of the capsule endoscope 2 is two (the capsule endoscopes 2a and 2b illustrated in FIG. 1) and, furthermore, the number of the receiving device 4 is five (the receiving devices 4a to 4e illustrated in FIG. 1). Furthermore, in FIG. 9, a description will be given of a state in a case where a user uses the receiving device 4a out of the receiving devices 4a to 4e and the capsule endoscope 2a. Furthermore, in general, if the user actually uses one of the receiving devices 4a to 4e, the user selects the one that has already been charged.

As illustrated in FIG. 9, first, the second control unit 65 determines whether the acquiring unit 61 has acquired the capsule ID (Step S201). If it is determined, by the second control unit 65, that the acquiring unit 61 has acquired the capsule ID (Yes at Step S201), the endoscope system 1 moves to Step S202, which will be described later. In contrast, if it is determined, by the second control unit 65, that the acquiring unit 61 has not acquired the capsule ID (No at Step S201), the second control unit 65 continues this determination.

At Step S202, the second control unit 65 determines whether the acquiring unit 61 has acquired the patient ID. Specifically, the second control unit 65 determines whether the user has read the patient ID attached to the subject by using the acquiring unit 61. If it is determined, by the second control unit 65, that the acquiring unit 61 has acquired the patient ID (Yes at Step S202), the endoscope system 1 moves to Step S203, which will be described later. In contrast, if it is determined, by the second control unit 65, that the acquiring unit 61 has not acquired the patient ID (No at Step S202), the second control unit 65 continues this determination.

Figure 10:
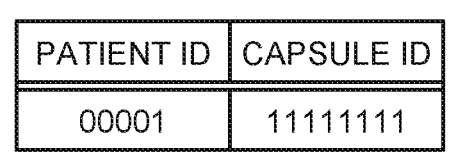

At Step S203, the second control unit 65 associates the capsule ID with the patient ID both of which have been acquired by the acquiring unit 61. For example, as illustrated in FIG. 10, the second control unit 65 associates the capsule ID (11111111) with the patient ID (00001) that have been acquired by the acquiring unit 61 and then records the associated information in the second recording unit 64.

Subsequent Step S204 to Step S206 are associated with above described Step S101 to Step S103, respectively, illustrated in FIG. 4. After having performed communication establishment between the receiving device 4a and the capsule endoscope 2a, an examination of the user is started by allowing the subject to orally swallow the capsule endoscope 2a.

Then, the second control unit 65 determines whether the examination of the subject has been ended (Step S207). Specifically, by determining whether image data has been transferred from the receiving device 4a, the second control unit 65 determines whether the examination of the subject has been ended. In this case, if the transfer of the image data from the receiving device 4a is started, the second control unit 65 determines that the examination of the subject has been ended. Of course, the second control unit 65 may also determine whether the examination of the subject has been ended based on a method other than this, such as based on, for example, an end signal indicating that the examination of the subject input from the second input unit 62, or may also determine whether the examination of the subject has been ended when predetermined set time (for example, 24 hours) elapses. If it is determined, by the second control unit 65, that the examination of the subject has been ended (Yes at Step S207), the endoscope system 1 moves to Step S208, which will be described later. In contrast, if it is determined, by the second control unit 65, that the examination of the subject has not been ended (No at Step S207), the second control unit 65 continues this determination.

At Step S208, the searching unit 651 searches for, based on the capsule ID acquired by the acquiring unit 61, from among the plurality of the receiving devices 4a to 4e connected to the workstation 6, the receiving device 4a that records therein the same capsule ID as that acquired by the acquiring unit 61.

Subsequently, if it is determined, by the searching unit 651, that the receiving device 4a associated with the capsule ID acquired by the acquiring unit 61 is present (Yes at Step S209), the second control unit 65 performs a process for associating the capsule ID, which is associated with the patient ID recorded in the second recording unit 64 in the workstation 6, with the capsule ID, which has been recorded in the first recording unit 45 in the receiving device 4a (Step S210). After Step S210, the endoscope system 1 ends the process.

At Step S209, if it is determined, by the searching unit 651, that the receiving device 4a associated with the capsule ID acquired by the acquiring unit 61 is not present (No at Step S209), the workstation 6 returns to Step S208.

According to the second embodiment described above, because, after the end of the examination of the subject, a process for associating the capsule ID, which has been associated with the patient ID recorded in the workstation 6, with the capsule ID, which has been recorded in the receiving device 4, is performed on the receiving device 4, the initialization process is performed after the examination even under the condition that the initialization process is not able to be performed on the receiving device 4, such as under the condition of, for example, an urgent examination to be performed on a subject by using the capsule endoscope 2. Thus, even in a case where one of the plurality of the receiving devices 4a to 4e is used, it is possible to efficiently perform the initialization process.

Third Embodiment

In the following, a third embodiment according to the present disclosure will be described. The third embodiment is different from the first embodiment described above in that the configuration of the workstation 6 is different and the process performed by the endoscope system is different. Specifically, in the first embodiment described above, an examination of a subject is started after having performed the initialization process on the receiving device; however, in the third embodiment, after having transmitted examination information, such as a patient ID, to all of the receiving devices connected to the workstation and allowing the state to be a temporary initialization state by performing a temporary initialization process, the initialization process is performed on the receiving device that is associated with the capsule ID of the capsule endoscope and then the examination of the subject is started. Consequently, in a description below, after having described the configuration of the workstation used for the capsule endoscope according to the third embodiment, the process performed by the capsule endoscope system according to the third embodiment will be described. Furthermore, components that are identical to those in the endoscope system 1 according to the first embodiment are assigned the same reference numerals and descriptions thereof will be omitted.

Configuration of Workstation

Figure 11:
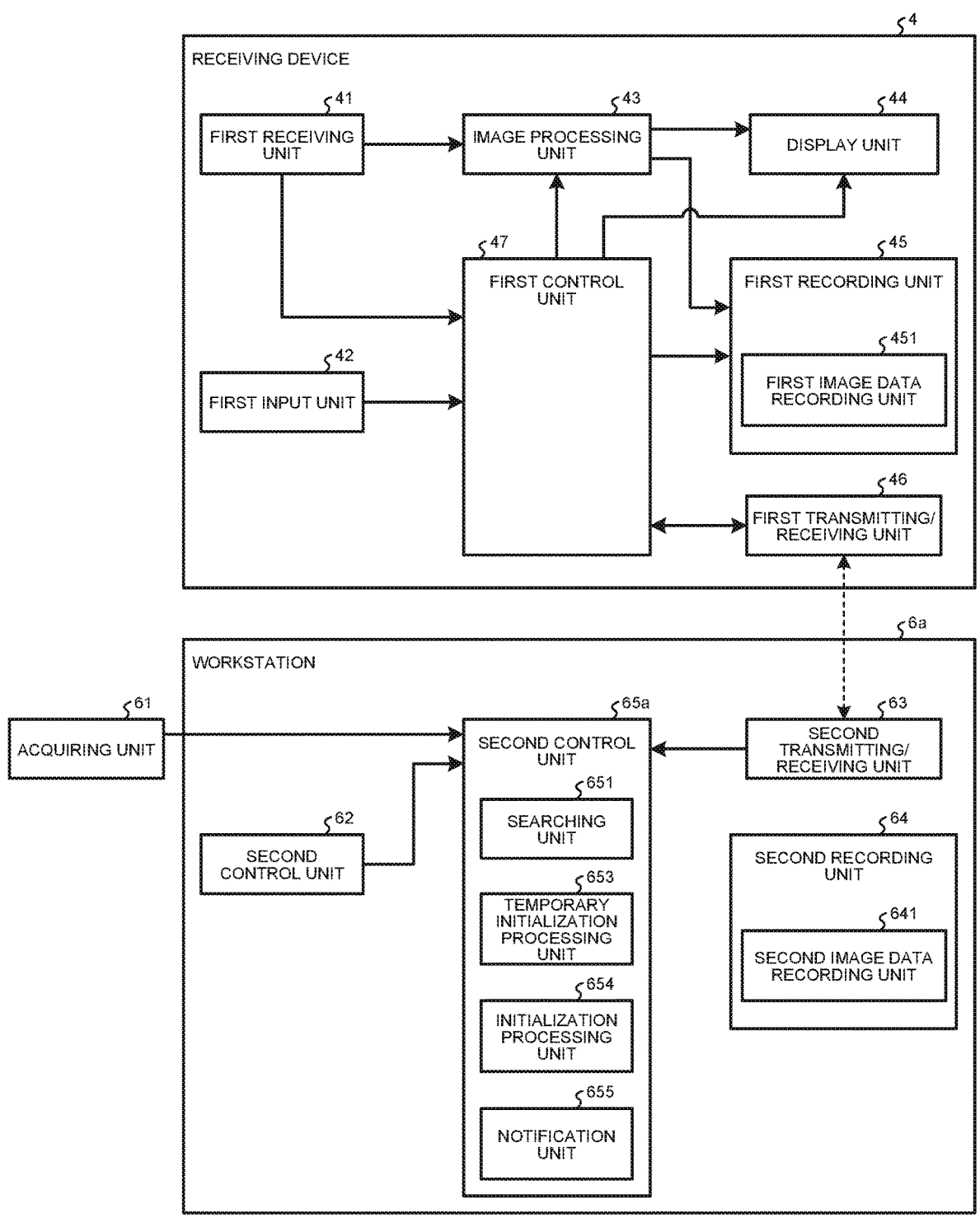
FIG. 11 is a block diagram illustrating a functional configuration of a receiving device and a workstation according to a third embodiment.

FIG. 11 is a block diagram illustrating a functional configuration of a receiving device and a workstation according to a third embodiment. A workstation 6a illustrated in FIG. 11 includes a second control unit 65a instead of the second control unit 65 included in the workstation 6 according to the first embodiment described above.

The second control unit 65a controls an operation of each of the units included in the workstation 6a. The second control unit 65a is constituted by using a CPU or the like. The second control unit 65a includes the searching unit 651, a temporary initialization processing unit 653, and an initialization processing unit 654.

If the acquiring unit 61 has acquired a capsule ID, the temporary initialization processing unit 653 performs a temporary initialization process for allowing each of the plurality of the receiving devices 4a to 4e to record the same patient ID as that acquired by the acquiring unit 61.

The initialization processing unit 654 performs an initialization process for associating the patient ID of the subject with the image data on the receiving device 4 in which the temporary initialization process has been performed by the temporary initialization processing unit 653 and wireless communication has been established with the capsule endoscope 2 and that has been specified according to a search result obtained by the searching unit 651.

A notification unit 655 transmits the capsule ID of the capsule endoscope 2 that has established the wireless communication with the receiving device 4 to the receiving device 4 that has not established wireless communication with the capsule endoscope 2. For example, if the receiving device 4a and the capsule endoscope 2a have established wireless communication, the notification unit 655 transmits the capsule ID of the capsule endoscope 2a to the other receiving devices 4b to 4e.

Process performed by Capsule Endoscope System

Figure 12:
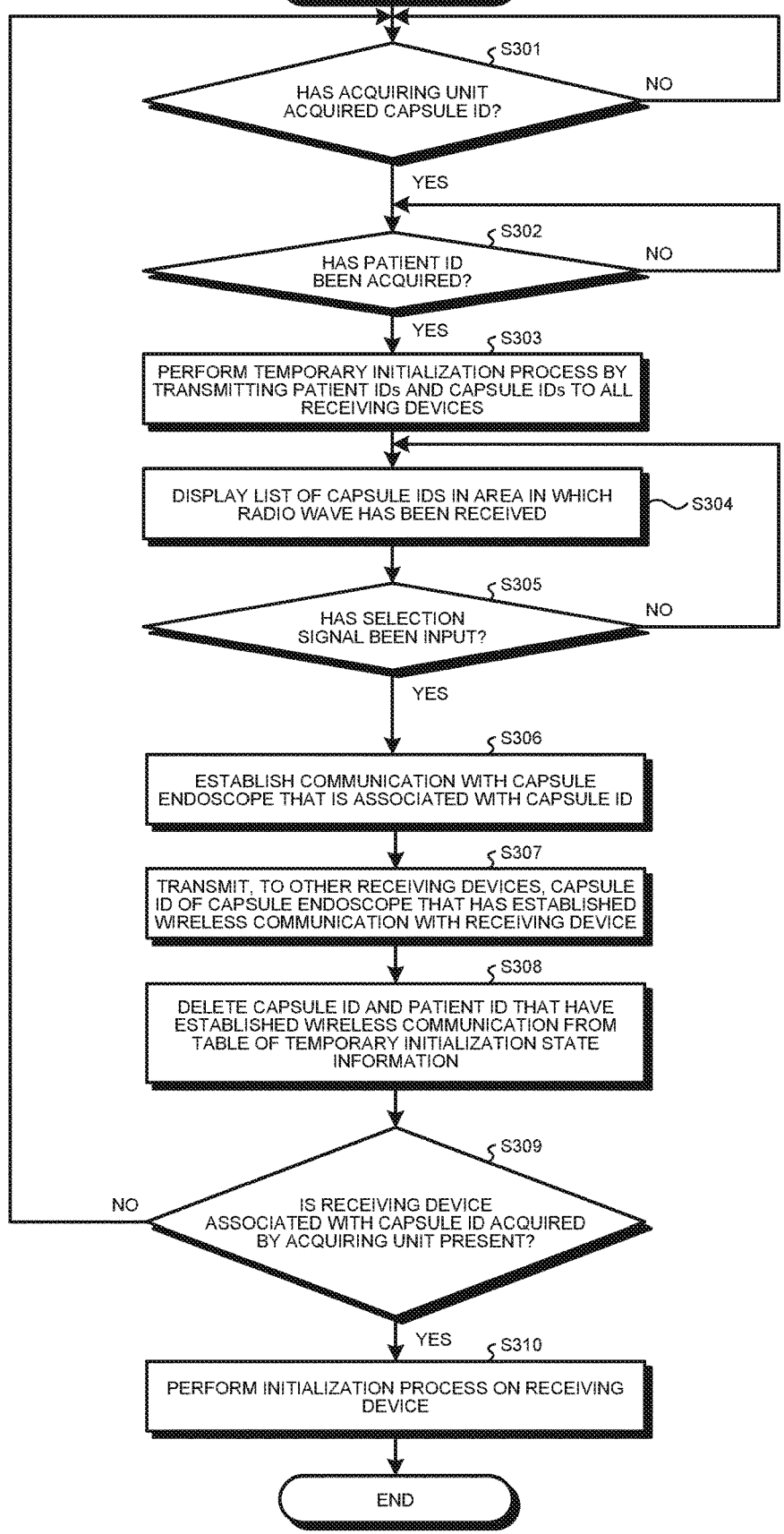
FIG. 12 is a flowchart illustrating an outline of a process performed by an endoscope system according to the third embodiment.

In the following, the process performed by the endoscope system 1 will be described. FIG. 12 is a flowchart illustrating an outline of the process performed by the endoscope system 1. Furthermore, in FIG. 12, a description will be given of a case in which the number of the capsule endoscopes 2 is two (the capsule endoscopes 2a and 2b illustrated in FIG. 1) and, furthermore, the number of the receiving devices 4 is five (the receiving devices 4a to 4e illustrated in FIG. 1). Furthermore, in FIG. 12, a description will be given of a state in a case where a user uses the receiving device 4a out of the receiving devices 4a to 4e and the capsule endoscope 2a. Furthermore, in general, if the user actually uses one of the receiving devices 4a to 4e, the user selects the one that has already been charged.

Step S301 and Step S302 are associated with Step S201 and Step S202, respectively, described above with reference to FIG. 9.

At Step S303, the temporary initialization processing unit 653 performs a temporary initialization process for allowing each of the plurality of the receiving devices 4a to 4e to enter a temporary initialization state by transmitting patient IDs and capsule IDs that are different with each other. In this case, the first control unit 47 transmits, for example, as illustrated in FIG. 13, the patient ID (00001) and the capsule ID (11111111) and displays, on the display unit 44, temporary initialization state information T30 in which the status is "temporary". Consequently, the user may intuitively grasp the state in which each of the plurality of the receiving devices 4a to 4e enters the temporary initialization state.

Step S304 to Step S306 are associated with Step S101 to Step S103, respectively, described above with reference to FIG. 4. In this case, the first control unit 47 displays, for example, as illustrated in FIG. 14, state information T31, in which the status is "official" on the display unit 44 by transmitting "00001" as the patient ID and "11111111" as the capsule ID.

At Step S307, if the receiving device 4a and the capsule endoscope 2a have established wireless communication, the notification unit 655 transmits, to the other receiving devices 4b to 4e, the capsule ID of the capsule endoscope 2a that has established wireless communication with the receiving device 4a.

Subsequently, the first control units 47 in the other receiving devices 4b to 4e delete the capsule ID and the patient ID that have established the wireless communication from the table of the temporary initialization state information T40 and then display the result on the display units 44 (Step S308). For example, as illustrated in FIG. 15, the first control units 47 in the other receiving devices 4b to 4e delete the capsule ID (11111111) of the capsule endoscope 2a and the patient ID (00001) from the table of the temporary initialization state information T40 and display the result on the display units 44. Consequently, when a user performs an examination of the subject by using the other receiving devices 4b to 4e, it is possible for the user to prevent erroneous selection of the capsule endoscope 2 or the receiving device 4 in which setting of communication establishment has been completed. Furthermore, the first control unit 47 in the receiving device 4a that has been established communication with the capsule endoscope 2a may also display, as illustrated in FIG. 16, only the patient ID (00001) and the capsule ID (11111111) having the status of "official".

Subsequently, if it is determined, by the searching unit 651, that the receiving device 4a associated with the capsule ID acquired by the acquiring unit 61 is present (Yes at Step S309), the initialization processing unit 654 performs the initialization process on the receiving device 4a (Step S310).

At Step S309, if it is determined, by the searching unit 651, that the receiving device 4a associated with the capsule ID acquired by the acquiring unit 61 is not present (No at Step S309), the workstation 6a returns to Step S301.

According to the third embodiment described above, it is possible to efficiently perform the initialization process even when one of the plurality of the receiving devices 4a to 4e is used.

Other Embodiments

The present disclosure is not limited to the embodiments described above and various modifications and applications are, of course, possible as long as they do not depart from the spirit. For example, in addition to the endoscope system used for explanation, the present disclosure may be used for a server that distributes moving images to mobile phones and smart phones via a network, a network-attached storage (NAS), a video camera, an endoscope, a monitoring camera, and an apparatus, such as an imaging device capable of performing bidirectional communication with a network by way of an optical apparatus, such as a microscope.

Furthermore, in the explanation of each operation flowchart described above in this document, the operations are described using "first", "then", "subsequently", "thereafter", and the like; however, this does not mean that it is necessary to perform the operations in this order.

Furthermore, the technique of each of the processes performed by the terminal device and the server according to the embodiment described above, i.e., the process indicated by each of the flowchart, may be stored as programs executed by a control unit, such as a CPU. Furthermore, the process may also be stored in a storage medium of an external storage device, such as a memory card (a ROM card, a RAM card, or the like), a magnetic disk, a hard disk, an optical disk (a CD-ROM, a DVD, or the like), or a semiconductor memory, and then distributed. Then, the control unit, such as a CPU, reads the program stored in the storage medium of the external storage device and the operations are controlled by the read program, thereby the processes described above may be executed.

Furthermore, the present disclosure is not limited to the above described embodiments and modifications as they are. In the implementation stage, the present disclosure may be embodied with various modifications of components as long as they do not depart from the scope of the disclosure. In addition, variations may be made by appropriately combining a plurality of components disclosed in the above embodiments. For example, some components may be deleted from all of the components described in the embodiments and the modifications described above. Furthermore, the components described in the embodiments and the modifications may be appropriately combined.

According to the present disclosure, an advantage is provided in that it is possible to efficiently perform an initialization process even when one of a plurality of receiving devices is used.

Moreover, in the specification or the drawings, a term that is at least once described together with a different term having a broader meaning or the same meaning may be replaced with the different term at any point in the specification or the drawings. Thus, various modifications and applications may be made without departing from the scope of the disclosure.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
    a capsule endoscope that is capable of being introduced into a subject and that wirelessly transmits image data obtained by capturing an image inside the subject;
    a plurality of receiving devices each of which receives and records the image data wirelessly transmitted by the capsule endoscope, each of the receiving devices including
        a receiver configured to receive, by using wireless communication, identification information for identifying the capsule endoscope,
        a recorder configured to record the image data, and
        a first controller configured to establish wireless communication with the capsule endoscope according to a reception result of the receiver and record, in the recorder, the image data transmitted from the capsule endoscope by associating the image data with the identification information of the capsule endoscope; and
    a workstation that is connected to the plurality of the receiving devices, the workstation including
        a processor comprising hardware, the processor being configured to execute
            acquiring, from a recording medium that records the identification information attached to the capsule endoscope, the identification information and subject identification information for identifying the subject,
            searching for the receiving device that has recorded the same identification information as the acquired identification information, and
            performing, on the receiving device specified according to a search result obtained by the searching, an initialization process for associating the subject identification information with the image data.

2. The endoscope system according to claim 1, wherein
    a plurality of the capsule endoscopes are present,
    the workstation further includes a transmitter configured to transmit the identification information of the capsule endoscope that has established wireless communication with one of the receiving devices to another receiving devices that has not established wireless communication with the capsule endoscope,
    each of the receiving devices further includes a display configured to display a plurality of pieces of the identification information, and
    in a case where the one of the receiving devices does not establish wireless communication with any of the plurality of the capsule endoscopes, when the one of the receiving devices receives, from the transmitter, the identification information of the capsule endoscope that has established wireless communication with the other receiving device, the first controller deletes the identification information of the capsule endoscope that has established wireless communication with the other receiving device from the plurality of pieces of the identification information displayed by the display.

3. The endoscope system according to claim 2, wherein each of the receiving devices further includes an input device configured to receive an input of a selection signal for selecting one of the plurality of pieces of the identification information displayed by the display, and the first controller establishes wireless communication with the capsule endoscope in which the identification information associated with the selection signal has been attached.

4. The endoscope system according to claim 1, wherein the processor of the workstation further execute
performing a temporary initialization process for allowing each of the plurality of receiving devices to record the same subject identification information, and
performing the initialization process on the receiving device in which the temporary initialization process has been performed by the processor and wireless communication has been established with the capsule endoscope and that has been specified according to the search result obtained by the searching.

5. A workstation to which a plurality of receiving devices each of which receives and records image data wirelessly transmitted from a capsule endoscope is connected so as to perform communication, the workstation comprising:
a processor comprising hardware, the processor being configured to execute
acquiring, from a recording medium that records identification information attached to the capsule endoscope, the identification information and subject identification information for identifying the subject;
searching for the receiving device that has recorded the same identification information as the acquired identification information; and
performing, on the receiving device specified according to a search result obtained by the searching, an initialization process for associating the subject identification information with the image data.

6. The workstation according to claim 5, wherein the processor further executes performing a temporary initialization process for allowing each of the plurality of the receiving devices to record the same subject identification information, wherein
the processor performs the initialization process on the receiving device in which the temporary initialization process has been performed by the processor and wireless communication has been established with the capsule endoscope and that has been specified according to the search result obtained by the searching.

7. The workstation according to claim 5, further comprising a transmitter configured to transmit the identification information of the capsule endoscope that has established wireless communication with one of the receiving devices to another receiving device that has not established wireless communication with the capsule endoscope.

8. A setting method performed by an endoscope system that includes
a capsule endoscope that is capable of being introduced into a subject and that wirelessly transmits image data obtained by capturing an image inside the subject,
a plurality of receiving devices each of which receives and records the image data wirelessly transmitted by the capsule endoscope, and
a workstation that is connected to the plurality of the receiving devices, the setting method comprising:
acquiring, from a recording medium that records identification information attached to the capsule endoscope, the identification information and subject identification information for identifying the subject;
searching for the receiving device that has recorded the same identification information as the acquired identification information; and
performing, on the receiving device that has been specified according to a search result obtained at the searching, an initialization process for associating the subject identification information with the image data.

9. A non-transitory computer readable recording medium on which an executable program is recorded, the program instructing a processor of an endoscope system including
a capsule endoscope that is capable of being introduced into a subject and that wirelessly transmits image data obtained by capturing an image inside the subject,
a plurality of receiving devices each of which receives and records the image data wirelessly transmitted by the capsule endoscope, and
a workstation that is connected to the plurality of the receiving devices, to execute:
acquiring, from a recording medium that records identification information attached to the capsule endoscope, the identification information and subject identification information for identifying the subject;
searching for the receiving device that has recorded the same identification information as the acquired identification information; and
performing, on the receiving device that has been specified according to a search result obtained at the searching, an initialization process for associating the subject identification information with the image data.

* * * * *